(12) United States Patent
Hellberg

(10) Patent No.: US 7,081,138 B2
(45) Date of Patent: Jul. 25, 2006

(54) LOCK MECHANISM ON A PROSTHETIC DEVICE

(75) Inventor: Kennet Hellberg, Vallentuna (SE)

(73) Assignee: Centri AB, Jarfalla (SE)

( * ) Notice: Subject to any disclaimer, the term of this patent is extended or adjusted under 35 U.S.C. 154(b) by 44 days.

(21) Appl. No.: 10/312,253

(22) PCT Filed: Aug. 21, 2002

(86) PCT No.: PCT/SE02/01483

§ 371 (c)(1),
(2), (4) Date: Dec. 24, 2002

(87) PCT Pub. No.: WO03/041619

PCT Pub. Date: May 22, 2003

(65) Prior Publication Data

US 2004/0102856 A1    May 27, 2004

(30) Foreign Application Priority Data

Sep. 26, 2001   (SE) .................................. 01031863

(51) Int. Cl.
*A61F 2/80* (2006.01)

(52) U.S. Cl. ...................................................... 623/36

(58) Field of Classification Search .................. 623/33, 623/36–38, 34, 35
See application file for complete search history.

(56) References Cited

U.S. PATENT DOCUMENTS

| 55,645 | A | * | 6/1866 | Gilson ......................... 623/35 |
| 5,211,667 | A | | 5/1993 | Danforth |
| 5,507,837 | A | | 4/1996 | Laghi |
| 5,728,170 | A | | 3/1998 | Becker et al. |
| 6,440,173 | B1 | * | 8/2002 | Meyer ......................... 623/36 |
| 2003/0195636 | A1 | * | 10/2003 | Coop .......................... 623/36 |

FOREIGN PATENT DOCUMENTS

DE        3508919 A1    9/1986

* cited by examiner

*Primary Examiner*—David H. Willse
(74) *Attorney, Agent, or Firm*—Young & Thompson

(57) ABSTRACT

Lock mechanism for detachable connection of a prosthetic device to a sleeve element carried on the residuum of an amputee, comprising a locking pin (3,30,40,50) connected to the sleeve element and a seat (5) arranged on the prosthetic device, in which seat the locking pin is longitudinally inserted for arresting engagement with arresting elements (11,52). The locking pin (3,30,40,50) is flexible for bending at least in one plane coincident with the longitudinal axis of the locking pin, and is preferably also longitudinally elastic.

15 Claims, 3 Drawing Sheets

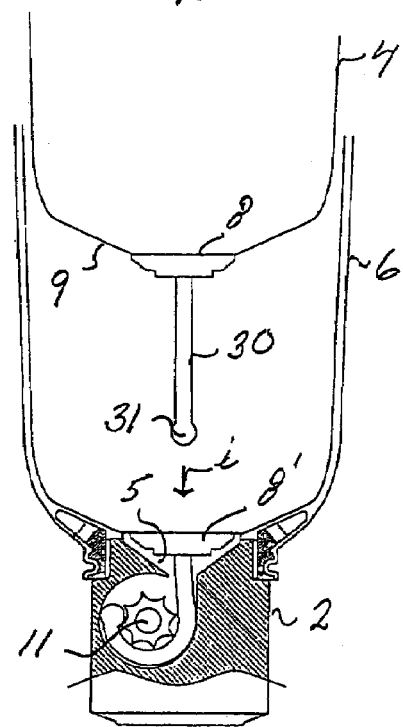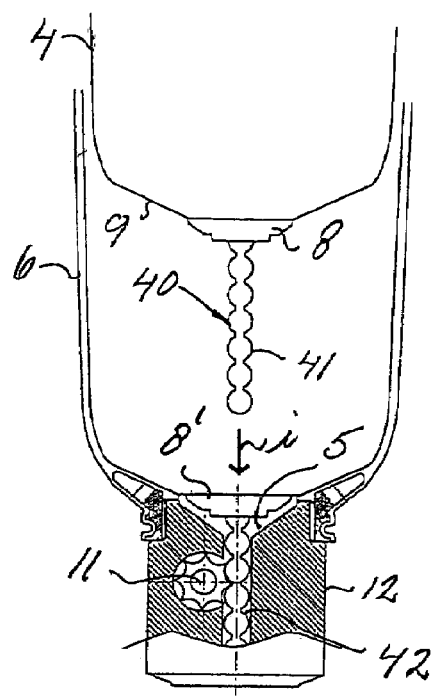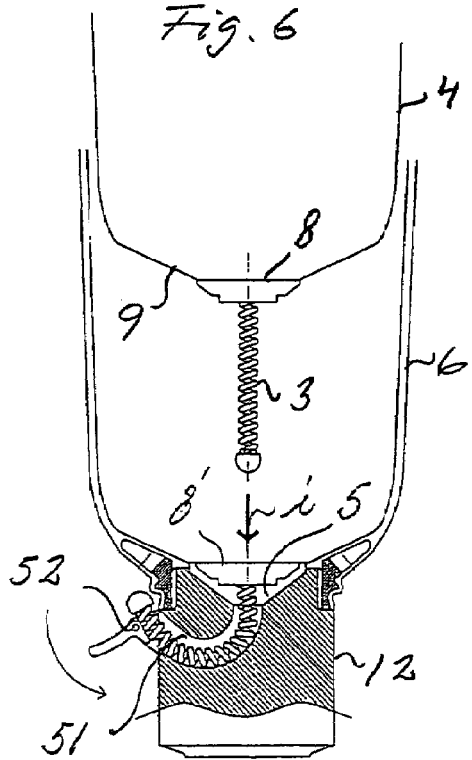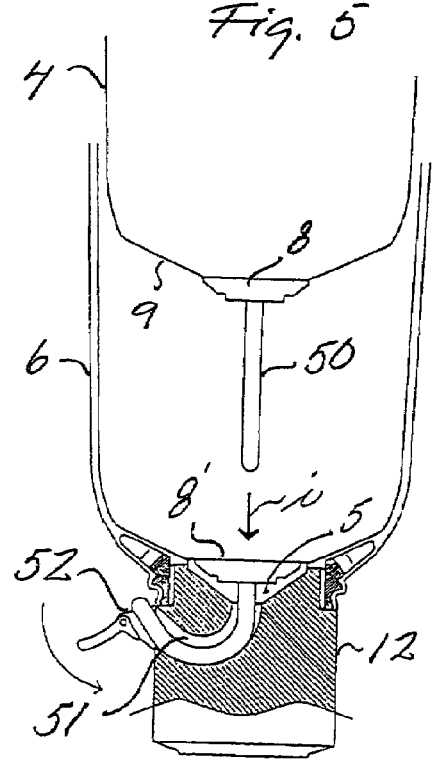

LOCK MECHANISM ON A PROSTHETIC DEVICE

TECHNICAL FIELD

Figure 1:
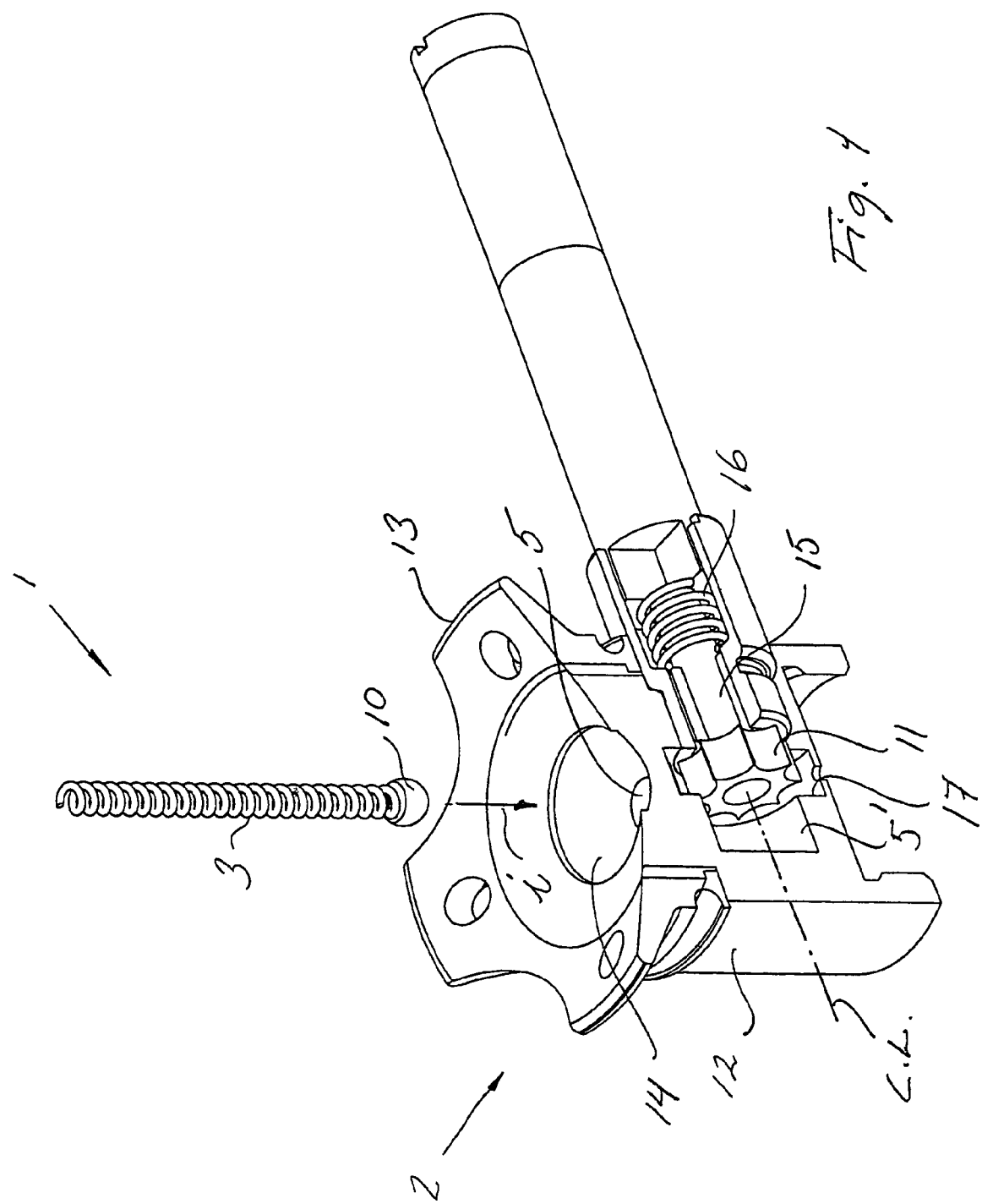

The invention refers to a lock mechanism for detachable connection of a prosthetic device to a sleeve element that is carried about an amputated limb.

BACKGROUND OF INVENTION AND PRIOR ART

The portion of a human extremity that remains after amputation is commonly referred to as an amputation stump or residuum. In the following disclosure the expression residuum is used with reference both to an amputated arm or an amputated leg. A prosthetic device, such as a leg prosthesis with or without a knee joint or an arm prosthesis with or without an elbow joint, may occasionally be attached to the residuum. A sleeve element that is carried about the amputated limb has a first member of a lock mechanism in the distal end of the sleeve. A second member of the lock mechanism is arranged on the prosthetic device for detachable connection of the prosthesis and the residuum.

In prior lock mechanisms the first member of the mechanism comprises a rigid locking pin, centrally arranged in the distal end of a flexible sleeve element that encompasses the end of the residuum. When connecting the prosthesis, the locking pin, usually made of steel, is inserted in a seat formed in the second member of the lock mechanism. The seat for the locking pin is formed in the bottom of a rigid socket element, adapted to the shape of the residuum. The prosthesis is carried on the rigid socket, and the socket transferring loads from the residuum to the prosthetic device via the lock mechanism.

A typical lock mechanism of this kind is disclosed in U.S. Pat. No. 5,507,837 (LAGHI), comprising a detachable, rigid locking pin that has external ribs and is arrested in the prosthesis by means of a toothed wheel which rotates in one direction only. By insertion of the locking pin, the toothed wheel is brought into rotation through the teeth engaging the ribs on the locking pin. Upon detachment of the locking pin, the toothed wheel is displaced from engagement with the ribs by manually applying a pressure that moves the toothed wheel to the side, transversely from the axis of the locking pin. Other examples of prior lock mechanisms for the same purpose may be found in U.S. Pat. No. 5,226,918 (SILAGY et al.), U.S. Pat. No. 5,888,234 (LITTIG et al.), U.S. Pat. No. 6,051,026 (PIRO et al.), e.g.

Previous lock mechanisms suffer from drawbacks that may occasionally cause discomfort for the wearer of the prosthesis. The present invention seeks to eliminate these drawbacks, drawbacks which may cause problems as will be more closely explained below.

The rigid and individually adapted socket, carrying the prosthesis, is formed as an inverted copy of the residuum. Since the shape of the residuum is strongly individual there is a problem, when adapting the socket, simultaneously to ensure that the locking pin's seat in the bottom of the socket is correctly centered and aligned with the locking pin. When dressing the soft sleeve onto the residuum there is also a risk that the locking pin in the distal end of the sleeve is positioned at the side of an ideal insertion direction relative to the seat, and/or at a slanting angle relative to the insert direction. In such case insertion of the locking pin becomes complicated, and discomforting pressure and tension loads will be transferred to the residuum that is connected to the prosthesis.

Another drawback associated with some of the conventional lock mechanisms is the relative building height. The height dimension is the result from an exaggerated length of the locking pin, the pin being used for pulling in the residuum into the rigid socket by operation of the lock mechanism. This functionality may be seen as an attempt to meet the problem of a tilted and wrongly aligned locking pin that is difficult to insert in the seat of the lock mechanism. However, this solution does not eliminate the problem of undesired loads acting on the residuum and caused by the locking pin deviating from an ideal insert direction. An exaggerated building height may also cause difficulties in adapting the prosthesis to the length of the residuum.

Yet another drawback related to some known lock mechanisms may be referred to the axial stiffness of the locking pin. Walking with a leg prosthesis causes the muscles and other soft tissue of the residuum to move in a pumping motion, sometimes leading to chafing caused by the rigid socket that encloses the residuum. This so called piston effect is made worse through the locking pin which has no axial elasticity. The combination of a long locking pin and radial forces generated from an inaccurate alignment relative to the seat may also cause the locking pin to be jammed in the seat, requiring a technician for removing the prosthesis.

SUMMARY OF THE INVENTION

The object of the present invention is to advise a lock mechanism that provides a solution to one or more of these and other problems associated with conventional lock mechanisms for detachable connection of a prosthesis to an amputation stump/residuum.

This object is met in a lock mechanism according to the appended claims, wherein advantageous embodiments are further defined in the subordinated claims.

Briefly, the invention foresees that a first member of the lock mechanism comprises a locking pin that is flexible in at least one plane coincident with the longitudinal axis of the locking pin. The second member of the lock mechanism comprises a seat having an arresting means for detachably arresting the locking pin. In some of the embodiments the arresting means may be controlled for pulling the locking pin into the seat, and thus forcing the residuum into the prosthetic device. In a preferred embodiment of the invention, the locking pin is formed from a coiled spring and the arresting means is a toothed wheel. Alternative embodiments comprise a locking pin made of elastic material such as synthetic rubber to be arrested in the prosthetic device by means of a clamping action, such as provided by an eccentric arresting means.

SHORT DESCRIPTION OF DRAWINGS

Figure 2:
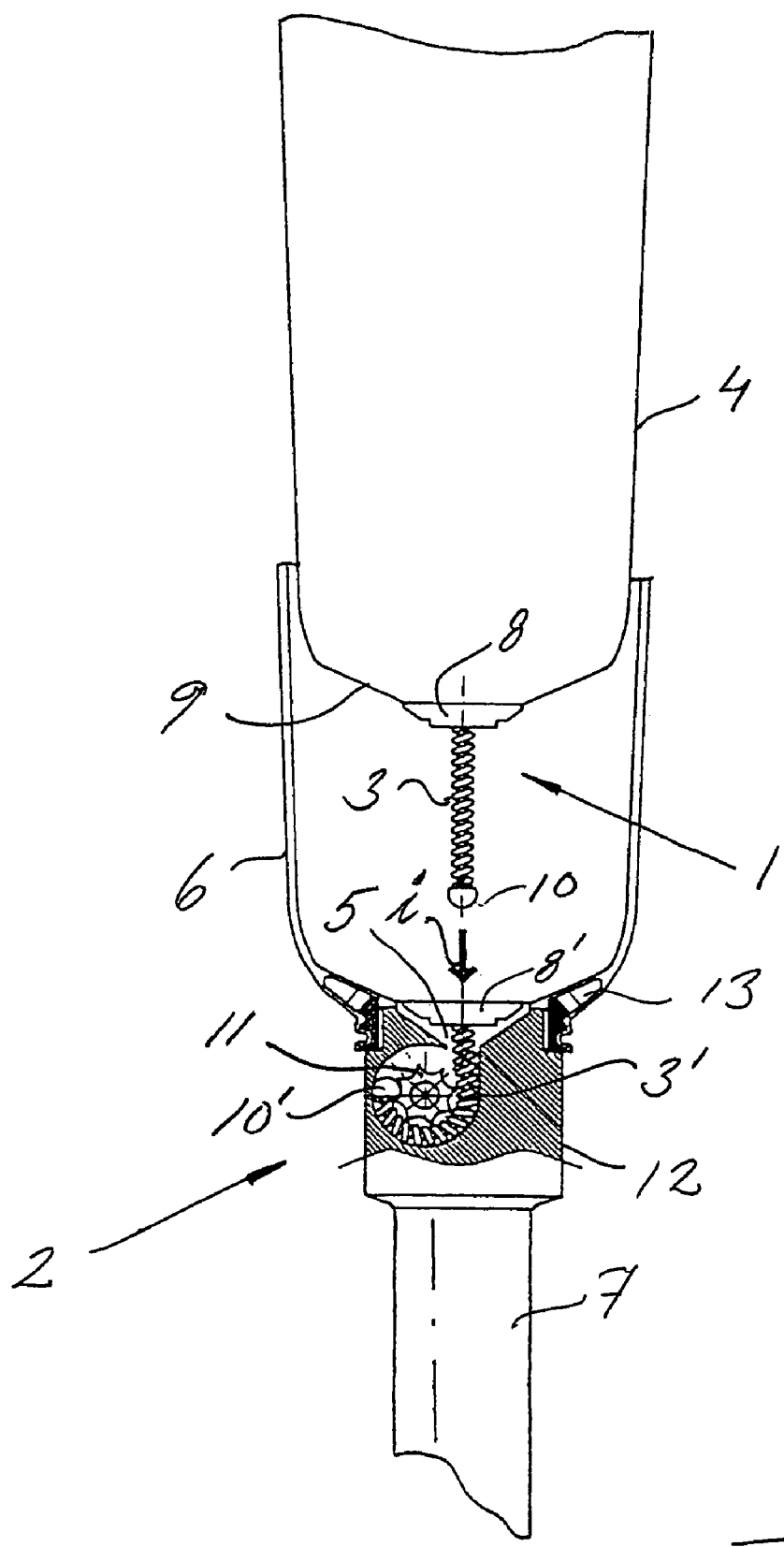

The invention will be more closely explained below in connection with exemplifying embodiments, and by reference to the attached schematic drawings wherein FIG. 1 is a partial perspective view of a lock mechanism according to the invention, and FIG. 2 is a sectional view through a prosthetic sleeve element having a lock mechanism according to the invention, and wherein the locking pin also is shown to engage a toothed wheel in the attached position of the prosthesis;

FIG. 3 showing a first alternative embodiment of the lock mechanism;

FIG. 4 showing a second alternative embodiment of the lock mechanism;

FIG. 5 showing a third alternative embodiment of the lock mechanism, and

FIG. 6 showing a fourth alternative embodiment of the lock mechanism.

DETAILED DESCRIPTION OF THE DRAWINGS

By reference to the drawings, the lock mechanism according to one embodiment comprises a first member 1 that is arranged for detachable connection to a second member 2. The first member 1 has a locking pin 3, extending from the distal end of a soft sleeve element 4 that is carried about an amputation stump/residuum (not shown). The second member 2 has a seat 5 arranged in a bottom of a rigid socket 6 that is connected to a prosthetic device 7 (shown herein as a prosthetic tube 7).

One end of the locking pin 3 is anchored in a disc 8, the disc being attached to a central area of the distal end 9 of the soft sleeve by being embedded, clamped, or fixed thereto in any other suitable way. The other and free end of the locking pin 3 carries a ball shaped body or a part-spherical body 10, that engages a toothed wheel 11 in the locked position of the lock mechanism as will be further explained below. In a preferred embodiment, the locking pin is a coil spring.

The second member 2 of the lock mechanism comprises a housing 12, formed with the seat 5 for the locking pin. The housing 12 is connected to, or integrally formed, with a flange 13 that is embedded in or otherwise attached to the bottom of the rigid socket 6. The seat 5 has an upper, conical portion 14 for guiding the locking pin towards the center axis i of the housing. Longitudinally below the conical guide portion 14 the seat 5 opens into a cylindrical chamber. The center axis CL of the cylindrical chamber runs transversely to the center axis of the housing, and laterally displaced there from. The toothed wheel 11 is carried on a rod 15 that is supported in the housing with the longitudinal axis of the rod being coincident with the center axis CL of the cylindrical chamber of the seat. The diameter of the toothed wheel is determined relative to the locking pin and the diameter of the cylindrical chamber, such that the locking pin may bend about the periphery of the toothed wheel, between the toothed wheel and the cylindrical wall of the seat as is illustrated at 3' in FIG. 2.

The toothed wheel 11 is carried for rotation on the bar 15, but only for rotation with the insert direction of the locking pin. Upon insertion of the locking pin the ball shaped body 10 engages with the teeth of the toothed wheel for connecting the prosthesis to the residuum. The toothed wheel is brought to rotate with the insert direction of the locking pin as far as the residuum is seated in the bottom of the socket 6. The prosthesis is then arrested in this connected position by the toothed wheel engaging the ball shaped body and/or the locking pin 3. This is illustrated at 10' in FIG. 2. The toothed wheel 11 may also be rotated through manually rotating the bar 15 for pulling the locking pin 3 into the seat.

Detachment of the prosthetic device by disconnecting the locking pin 3 is accomplished through the bar 15 and toothed wheel 11 being axially displaceable, from an outer arresting position shown in FIG. 1 to a disconnecting position (not shown), against the force of a spring 16. A cylindrical extension 5' of the cylindrical chamber of the seat has a diameter that is dimensioned to receive the displaced toothed wheel in the disconnecting position. A shoulder 17, formed to be concentric with the seat 5, retains the locking pin in the seat such that the toothed wheel disengages the ball shaped body 10 and the locking pin is free to be disconnected and withdrawn from the housing 12.

The locking pin 3 is shaped as a coiled spring and flexible in all planes coincident with its longitudinal axis. In this way, an inaccurate alignment of the locking pin when dressing the soft sleeve on the residuum is widely compensated for since the locking pin is flexible in all directions and thus will not transfer heavy loads to the amputation site. The locking pin 3 is also elastically flexible in axial direction, which substantially reduces the so called piston effect that is involved with lock mechanisms having a rigid locking pin. The flexible locking pin allows for a lock mechanism designed with reduced building height, thus providing a universal mechanism for connecting a prosthetic device to the residuum and by which the length of the residuum is no longer critical when designing the prosthetic device.

An alternative lock mechanism comprises a locking pin (not shown) made of spring steel, e.g., and which is flexible at least in one plane coincident with the longitudinal axis of the locking pin. This alternative lock mechanism may in all other respects be identical with the embodiment described before.

With reference to FIGS. 3–6 alternative embodiments of the lock mechanism of the invention are illustrated. The same reference numbers are used throughout the description for identifying corresponding or identical elements, common to all embodiments.

Accordingly, FIG. 3 shows a lock mechanism comprising a flexible locking pin 30 made from synthetic material. The locking pin has a homogenous and continuous section, one end of the locking pin being formed to have a ball shaped body 31. The locking pin 30 is arrested in the housing 12 by engagement with a toothed wheel 11, substantially as described with reference to the previous embodiment. The locking pin 30 is flexible in all directions and has longitudinal elasticity, thus providing the same advantages and operation as the coil spring locking pin 3 described before.

FIG. 4 shows an alternative embodiment of the lock mechanism having a flexible locking pin 40 made from synthetic material. The locking pin 40 has a homogenous section but is however segmented, showing successive, spherical bulges 41 similar to a string of beads. The locking pin 40 is arrested in the housing 12 by engagement with a toothed wheel 11. The toothed wheel 11 is supported at one side of a straight insert hole 42 for engagement between the bulges 41 in the arrested position, wherein the locking pin 40 extends essentially aligned with the longitudinal direction of the prosthetic device.

FIG. 5 shows an alternative lock mechanism having a flexible locking pin 50 made from synthetic material. The locking pin 50 has a homogenous, continuous or segmented section. The locking pin 50 is arrested in a housing 12, formed with a through channel 51 mouthing in one side of the housing. A clamping means 52, preferably an eccentric clamp 52 is arranged on the exterior of the housing. The clamping means 52 is designed for applying a clamping force by which the locking pin 50 is arrested, such as by being clamped towards a portion of the mouth of the through channel, a portion specifically designed for this purpose.

FIG. 6 shows a lock mechanism substantially as the embodiment of FIG. 5, and wherein the locking pin is shaped as a coil spring.

Common to all embodiments is the flexibility of the locking pin, a flexibility which provides the advantages mentioned above relative to the conventional, rigid locking pins. Non-limiting examples of suitable elastic materials for the locking pin are synthetic rubbers, such as nitrile rubber having a Shore A hardness of about 60° or above, or a styrene block copolymer of corresponding hardness.

The appended claims shall be understood to encompass all above and other embodiments appearing to the skilled technician when guided by the present disclosure.

The invention claimed is:

1. A lock mechanism for detachable connection of a prosthetic device to a sleeve element configured to be carried about the residuum of an amputated arm or leg, comprising:
    a locking pin anchored in the sleeve element and extended from a distal end of the sleeve element, said locking pin comprising a flexible portion flexible in at least one plane coincident with a longitudinal axis of the locking pin;
    a seat having an arresting means supported on the prosthetic device and formed to receive the flexible portion of the locking pin being inserted in the seat; and
    said arresting means arranged to releasably engage the flexible portion of the locking pin in a connected position,
    wherein the locking pin is a coiled spring and flexible in any plane coincident with the longitudinal axis of the locking pin.

2. The lock mechanism of claim 1, wherein the locking pin is elastic in the longitudinal direction.

3. The lock mechanism of claim 2, wherein the locking pin is made of elastic material.

4. The lock mechanism of claim 1, wherein the locking pin is made of synthetic rubber.

5. The lock mechanism of claim 1, wherein, the seat has an arcuate shoulder, along which shoulder the locking pin bends when received in the seat.

6. The lock mechanism of claim 5, wherein the locking pin bends at least 90 degrees when received in the seat.

7. A lock mechanism for detachable connection of a prosthetic device to a sleeve element configured to be carried about the residuum of an amputated arm or leg, comprising:
    a locking pin anchored in the sleeve element and extended from a distal end of the sleeve element;
    a seat having an arresting means supported on the prosthetic device and formed to receive the locking pin for connection of the prosthetic device,
    the locking pin being inserted longitudinally in the seat for engagement with the arresting means arranged on the prosthetic device,
    said locking pin being flexible in at least one plane coincident with a longitudinal axis of the locking pin; and
    a wheel arranged in the seat for arresting the locking pin through engagement while the locking pin is bended around a portion of the periphery of the wheel.

8. The lock mechanism of claim 7, wherein said wheel is a toothed wheel, and the toothed wheel is rotatable in the insert direction of the locking pin when connecting the prosthetic device, non-rotatable in the arresting position of the locking pin, and laterally displaceable out of engagement with the locking pin for disconnection of the prosthetic device.

9. The lock mechanism of claim 8, wherein a ball shaped body is formed in a free end of the locking pin, the toothed wheel engaging the ball shaped body in the arrested position of the locking pin.

10. The lock mechanism of claim 8, wherein the locking pin is segmented on the exterior to provide exterior segments, and the toothed wheel engaging the segments in the arrested position of the locking pin.

11. The lock mechanism of claim 7, wherein the locking pin is made of synthetic rubber.

12. A lock mechanism for detachable connection of a prosthetic device to a sleeve element configured to be carried about the residuum of an amputated arm or leg, comprising:
    a locking pin anchored in the sleeve element and extended from the distal end of the sleeve element;
    a seat having an arresting means supported on the prosthetic device and formed to receive the locking pin for connection of the prosthetic device,
    the locking pin comprising a flexible portion being inserted longitudinally in the seat for engagement with the arresting means arranged on the prosthetic device,
    the flexible portion of said locking pin engaged with said arresting means being flexible in at least one plane coincident with a longitudinal axis of the locking pin,
    the seat having a curved surface along a depth thereof, the flexible portion of said locking pin, when being engaged in the seat, being bent by the curved surface along the longitudinal axis of the locking pin, and
    the flexible portion of the locking pin being arrested in the seat by a clamping force controlled from outside the prosthetic device for pressing the locking pin towards the seat.

13. The lock mechanism of claim 12, further comprising a clamp means arranged on the exterior of the prosthetic device for engagement with the engaged flexible portion of the locking pin, guided by the seat to protrude on the outside of the prosthetic device.

14. The lock mechanism of claim 12, wherein the locking pin is made of synthetic rubber.

15. The lock mechanism of claim 12, wherein the locking pin bends at least 90 degrees when engaged in the seat.

* * * * *